(12) United States Patent
Tanaka et al.

(10) Patent No.: US 11,266,619 B2
(45) Date of Patent: Mar. 8, 2022

(54) PHARMACEUTICAL COMPOSITION FOR ENHANCING ANTITUMOR EFFECT BY IMMUNE CHECKPOINT INHIBITOR

(71) Applicants: SBI Pharmaceuticals Co., Ltd., Tokyo (JP); National Center for Child Health and Development, Tokyo (JP)

(72) Inventors: Tohru Tanaka, Tokyo (JP); Hidenori Ito, Tokyo (JP); Ko Rii, Tokyo (JP)

(73) Assignees: SBI Pharmaceuticals Co., Ltd., Tokyo (JP); National Center for Child Health and Development, Tokyo (JP)

( * ) Notice: Subject to any disclaimer, the term of this patent is extended or adjusted under 35 U.S.C. 154(b) by 0 days.

(21) Appl. No.: 16/651,238

(22) PCT Filed: Nov. 28, 2018

(86) PCT No.: PCT/JP2018/043704
§ 371 (c)(1),
(2) Date: Mar. 26, 2020

(87) PCT Pub. No.: WO2019/107389
PCT Pub. Date: Jun. 6, 2019

(65) Prior Publication Data
US 2020/0297674 A1   Sep. 24, 2020

(30) Foreign Application Priority Data
Dec. 1, 2017 (JP) .............................. JP2017-231449

(51) Int. Cl.
| | |
|---|---|
| *A61K 31/197* | (2006.01) |
| *C07K 16/28* | (2006.01) |
| *A61K 33/26* | (2006.01) |
| *A61K 33/24* | (2019.01) |
| *A61K 33/30* | (2006.01) |
| *A61K 38/00* | (2006.01) |

(52) U.S. Cl.
CPC ............ *A61K 31/197* (2013.01); *A61K 33/24* (2013.01); *A61K 33/26* (2013.01); *C07K 16/2818* (2013.01); *C07K 16/2827* (2013.01); *A61K 33/30* (2013.01); *A61K 38/00* (2013.01)

(58) Field of Classification Search
CPC ...... A61K 31/197; A61K 33/26; A61K 33/30; A61K 38/00; C07K 16/2818; C07K 16/2827
See application file for complete search history.

(56) References Cited

U.S. PATENT DOCUMENTS

| | | | |
|---|---|---|---|
| 2006/0110383 A1 | 5/2006 | Honjo et al. | |
| 2010/0203056 A1 | 8/2010 | Irving et al. | |
| 2012/0134921 A1 | 5/2012 | Helland et al. | |
| 2014/0302173 A1 | 10/2014 | Tanaka et al. | |

FOREIGN PATENT DOCUMENTS

| | | |
|---|---|---|
| CN | 104066428 A | 9/2014 |
| EP | 2340821 A1 | 7/2011 |
| EP | 2767277 A1 | 8/2014 |
| JP | 2011016753 | 1/2011 |
| JP | 2012012305 A | 1/2012 |
| JP | 5611548 | 10/2014 |
| JP | 5885764 | 3/2016 |
| RU | 2527328 C2 | 8/2014 |
| RU | 2636023 C2 | 11/2017 |
| WO | 2013054756 A1 | 4/2013 |
| WO | 2015129535 | 9/2015 |
| WO | 2016187122 A1 | 11/2016 |
| WO | 2017103280 | 6/2017 |
| WO | 2017103283 | 6/2017 |

OTHER PUBLICATIONS

Berger et al. (J. Med. Chem. 2000, 43, 25, 4738-4746) (Year: 2000).*
Miura et al. "The Effect of 5-Aminolevulinic Acid on Cytochrome P450-Mediated Prodrug Activation" PLoS One, 10 (7):e0131793 (9 pages) (2015).
English translation of International Search Report corresponding to International Patent Application No. PCT/JP2018/043704 (2 pages) (dated Jan. 29, 2019).
English translation of Notification of Reasons for Rejection issued by the Japanese Patent Office for Japanese Patent Application No. 2019-524476 (4 pages) (drafting date: Jun. 17, 2019).
Hou et al. "5-aminolevulinic acid with ferrous iron induces permanent cardiac allograft acceptance in mice via induction of regulatory cells" The Journal of Heart and Lung Transplantation, 34(2):254-263 (2015).
Kee et al. "Immunotherapy of melanoma" European Journal of Surgical Oncology, 43(3):594-603 (2017).
Wang et al. "5-Aminolevulinic Acid-mediated Sonodynamic Therapy Reverses Macrophage and Dendritic Cell Passivity in Murine Melanoma Xenografts" Ultrasound in Medicine & Biology. 40(9):2125-2133 (2014).
Watanabe et al. "Fundamentals of the Tumor Immunotherapy" Journal of Kyoto Prefectural University of Medicine, 126(6):377-389 (2017) (English translation of abstract).
Decision to Grant a Patent end English translation thereof corresponding to Japanese Patent Application No. 2019-524476 (5 pages) (dated Oct. 7, 2019).
Swart et al. "Combination Approaches with Immune-Checkpoint Blockade in Cancer Therapy" Frontiers in Oncology, 6(233):1-16 (2016).

(Continued)

*Primary Examiner* — James D. Anderson
*Assistant Examiner* — William Y Lee
(74) *Attorney, Agent, or Firm* — Myers Bigel, P.A.

(57) ABSTRACT

The object of the invention is to provide a pharmaceutical composition for enhancing the antitumor effect by an immune checkpoint inhibitor. Provided is a pharmaceutical composition for enhancing the antitumor effect by an immune checkpoint inhibitor comprising 5-aminolevulinic acids (ALAs) as the active ingredient.

6 Claims, 2 Drawing Sheets

(56) References Cited

OTHER PUBLICATIONS

Thallinger et al. "Review of cancer treatment with immune checkpoint inhibitors" Wiener klinische Wochenschrift, 130:85-91 (2018).
Yang et al. "Aminolevulinic Acid-Based Tumor Detection and Therapy: Molecular Mechanisms and Strategies for Enhancement" International Journal of Molecular Sciences, 16:25865-25880 (2015).
Chamoto et al. "Mitochondrial activation chemicals synergize with surface receptor PD-1 blockade for T cell-dependent antitumor activity" Proceedings of the National Academy of Sciences USA, 114(5):E761-E770 (2017).
Hou et al. "5-Aminolevulinic acid combined with ferrous iron induces carbon monoxide generation in mouse kidneys and protects from renal ischemia-reperfusion injury" American Journal of Physiology-Renal Physiology, 305(8):F1149-F1157 (2013).
Marquez-Rodas et al. "Immune checkpoint inhibitors: therapeutic advances in melanoma" Annals of Translational Medicine, 3(18):267, pp. 1-16 (2015).
Pardoll, Drew M. "The blockade of immune checkpoints in cancer immunotherapy" Nature Reviews Cancer, 12(4):252-264 (2016).
Zhao et al. "5-Aminolevulinic acid combined with sodium ferrous citrate ameliorates $H_2O_2$-induced cardiomyocyte hypertrophy via activation of the MAPK/Nrf2/HO-1 pathway" The American Journal of Physiology: Cell Physiology, 308(8):C665-C672 (2015).
De Siervi et al. "[delta]-Aminolevulinic acid cytotoxic effects on human hepatocarcinoma cell lines" BMC Cancer, 2 (1):1-6 (2002).
Extended European Search Report corresponding to European Patent Application No. 18882989.9 (10 pages) (dated May 7, 2021).
Watase et al. "Effect on immune checkpoint factors of photodynamic therapy in combination with aminolevulinic acid against malignant glioma" Nihon Ika Daigaku Igakkai Zasshi, 13(4):248, p. 20 (2017) (English translation).
Hu et al. "5-Aminolevulinic acid/sodium ferrous citrate enhanced the antitumor effects of programmed cell death-ligand 1 blockade by regulation of exhausted T cell metabolism in a melanoma model" Cancer Science, 00:1-12 (2021).
Peng et al. "Sonodynamic therapy improves anti-tumor immune effect by increasing the infiltration of CD8+ T cells and altering tumor blood vessels in murine B16F10 melanoma xenograft" Oncology Reports, 40:2163-2170 (2018).

\* cited by examiner

PHARMACEUTICAL COMPOSITION FOR ENHANCING ANTITUMOR EFFECT BY IMMUNE CHECKPOINT INHIBITOR

TECHNICAL FIELD

The present invention relates to a novel use of 5-aminolevulinic acid (hereinafter also simply referred to as "ALA") or a derivative thereof, specifically to the use of 5-aminolevulinic acid or a derivative thereof for enhancing the antitumor effect by an immune checkpoint inhibitor.

BACKGROUND ART

Tumors that had emerged in the human body are removed by the ordinarily inherent immune mechanism before they proliferate to an extent that they have harmful effects on the human body. The following phenomenon is known as this mechanism. Namely, a protein (tumor antigen) specific to cancer cells binds to a protein called class I MHC molecule in cancer cells, and is presented on the cell surface. When this class I MHC and the tumor antigen binds to the TCR (T Cell Receptor) protein on the surface of T cells which are responsible for immunity, the T cell recognizes this cell as a cancer cell. The T cell which recognized the cancer cell initiates proliferation, and damages the cancer cell presenting the tumor antigen.

However, it is known that when the cancer cell was expressing a membrane protein called PD-L1 together with class I MHC, by binding with a membrane protein called PD-1 which is being expressed in the T cell, the activation of the above T cell is suppressed. Because this cancer cell which has acquired the immunological escape mechanism which is normally for suppressing excess immunity continues to proliferate, inhibition of the binding between PD-L1 and PD-1 has been focused as the target for a new anticancer agent (Patent Literature 1). Note that PD-L1 is also expressed in "professional antigen-presenting cells" such as dendritic cells which specialize in presenting antigens to T cells. In recent years, anti-PD-1 antibodies nivolumab (Opdivo®) and pembrolizumab (Keytruda®) have been developed and put to practical use as anticancer agents, and anti-PD-L1 antibodies atezolizumab, durvalumab, avelumab (Bavencio™), and the like have also been developed and put to practical use.

On the other hand, in the antigen presentation of cancer cells (or professional antigen-presenting cells) to T cells, other mechanisms to suppress immune reaction (immune checkpoints) are also known, a representative of which is a combination of the B7 family molecule on the antigen-presenting side and CTLA4 on the T cell side, and pharmaceuticals such as ipilimumab (Yervoy®) and tremelimumab have been developed. In addition, CD137L-CD137, MHC-LAG-3/KIR, CD48-CD244, GAL9-TIM3, HVEM-BTLA/CD160, CD40L-CD40, OX40L-OX40, GITRL-GITR, and the like are known (in all of which the former is the molecule on the antigen-presenting side) (Non-Patent Literatures 1 and 2).

Recently, there has been a report that the antitumor effect by an anti-PD-1 antibody is related to the generation of reactive oxygen in T cells, and that the said antitumor effect is enhanced by intracellular signal transduction and mitochondrial activation by addition of a reactive oxygen generator at a low concentration. Moreover, it is reported at the same time that the antitumor effect of an anti-PD-1 antibody is also enhanced in pharmaceuticals that mimics this intracellular signal transduction (Non-Patent Literature 3).

The present inventors have found that an ALA or a derivative thereof is effective for cancer therapy by a presumed mechanism which enhances the heme or cytochrome in the mitochondria of a cancer cell or a cell almost becoming a cancer cell having formed an abnormality in the nucleus, improves mitochondrial activities such as the electron transport chain and the TCA cycle, and calls up the Bax and Bak systems to cause a caspase IX-type apoptosis when there is an abnormality in the nucleus that cannot be restored (Patent Literature 2).

On the other hand, ALA together with an arbitrary sodium ferrous citrate (SFC) becomes a heme in the body, and this heme is degraded by an enzyme called a heme oxygenase 1 (HO-1) to change into bilirubin and carbon monoxide (Non-Patent Literature 4). It is known that this bilirubin and carbon monoxide has a high antioxidant action and can directly/indirectly erase reactive oxygen species (ROS) (Non-Patent Literature 5)

Moreover, ALA, together with an arbitrary SFC, is known to have an immunological tolerance effect which suppresses immunity. This mechanism is thought to be where, in a dendritic cell which is the antigen-presenting cell, the above-described HO-1 (or bilirubin and carbon monoxide) changes (differentiates) the dendritic cell into a cell called a tolerogenic dendritic cell. A tolerogenic cell is known to highly express PD-L1 and to perform specific immunological tolerance (immunosuppression) on the antigen presented on the T cell, and in fact, a rise in the mRNA of PD-L1 has been observed in a cell that is recognized as a dendritic cell by administration of ALA and SFC (Non-Patent Literature 6).

CITATION LIST

[Patent Literature 1] JP Patent No. 5885764
[Patent Literature 2] JP Patent No. 5611548
[Non-Patent Literature 1] Nat Rev Cancer. 2012 Mar. 22; 12(4): 252-64.
[Non-Patent Literature 2] Ann Transl Med. 2015 October; 3(18): 267.
[Non-Patent Literature 3] Proc Natl Acad Sci USA. 2017 Jan. 31; 114(5): E761-E770.
[Non-Patent Literature 4] Am J Physiol Renal Physiol. 2013 Oct. 15; 305(8)F1149-57
[Non-Patent Literature 5] Am J Physiol Cell Physiol. 2015 Apr. 15; 308(8)C665-72.
[Non-Patent Literature 6] J Heart Lung Transplant. 2015 February; 34(2): 254-63.

SUMMARY OF THE INVENTION

Problems to be Solved by the Invention

As described above, cancer therapy agents that comprise an anti-PD-1 antibody or an anti-PD-L1 antibody as the active ingredient have been created, and further, a combination therapy method of these cancer therapy agents and preexisting pharmaceuticals has been drawing attention. In fact, a clinical trial of the combination of pharmaceuticals that mimic the above signal transduction (lipid-lowering drug bezafibrate that activates the transcription factor PPARs) and an anti-PD-1 antibody has been planned. Namely, there is a demand for the search or creation of a medicament or a pharmaceutical composition which has high correlation with immune checkpoint inhibitors such as an anti-PD-1 antibody or an anti-PD-L1 antibody and which may enhance the antitumor effect by an immune checkpoint inhibitor.

Accordingly, the object of the present invention is to provide a pharmaceutical composition for enhancing the antitumor effect by immune checkpoint inhibitors such as an anti-PD-1 antibody or an anti-PD-L1 antibody.

Means for Solving the Problems

As a result of repeated extensive investigation in order to solve the above problem, the present inventors found that 5-aminolevulinic acid (ALA) can significantly enhance the antitumor effect by an immune checkpoint inhibitor. As above, although ALA itself may be useful for cancer therapy, in consideration of the high antioxidant action by bilirubin and carbon monoxide (CO) resulting from administration of ALA or the immunological tolerance effect by ALA, when ALA is administered during cancer therapy by immune check inhibitors such as an anti-PD-1 antibody or an anti-PD-L1 antibody, it was rather thought that the effect of the immune checkpoint inhibitor will be counteracted due to ALA causing increase of PD-L1-expressing dendritic cells or reactive oxygen in T cells being removed by bilirubin and CO, and thus this result was surprising.

Namely, the present invention encompasses the following characteristics:

[1] A pharmaceutical composition for enhancing the antitumor effect of an immune checkpoint inhibitor, comprising the compound shown by the following Formula (I):

[Chemical Formula 1]

$R^1$—$NHCH_2COCH_2CH_2COOR^2$ (I), (wherein $R^1$ represents a hydrogen atom or an acyl group, and $R^2$ represents a hydrogen atom, a linear or branched alkyl group, a cycloalkyl group, an aryl group, or an aralkyl group) or a salt or an ester thereof.

[2] The pharmaceutical composition according to [1], wherein said immune checkpoint inhibitor is at least one selected from the group consisting of an anti-PD-1 antibody, an anti-PD-L1 antibody, an anti-CTLA4 antibody, an anti-B7 antibody, an anti-C27 antibody, an anti-KIR antibody, an IDO inhibitor, an anti-CD137 antibody, and an anti-TIM3 antibody.

[3] The pharmaceutical composition according to [2], characterized in that the immune checkpoint inhibitor is an anti-PD-L1 antibody or an anti-PD-1 antibody.

[4] The pharmaceutical composition according to [1], wherein said immune checkpoint inhibitor is selected from the group consisting of atezolizumab, durvalumab, avelumab, nivolumab, pembrolizumab, pidilizumab, BMS-936559, ipilimumab, tremelimumab, enoblituzumab, varlilumab, lirilumab, epacadostat, utomilumab, urelumab, and TSR-022.

[5] The pharmaceutical composition according to any of [1]-[4], characterized in that it is administered at the same time or at different times as the immune checkpoint inhibitor.

[6] The pharmaceutical composition according to any of [1]-[6], characterized in that:

$R^1$ is selected from the group consisting of a hydrogen atom, an alkanoyl group having 1-8 carbons, and an aroyl group having 7-14 carbons, and $R^2$ is selected from the group consisting of a hydrogen atom, a linear or branched alkyl group having 1-8 carbons, a cycloalkyl group having 3-8 carbons, an aryl group having 6-14 carbons, and an aralkyl group having 7-15 carbons.

[7] The pharmaceutical composition according to any of [1]-[7], wherein $R^1$ and $R^2$ are hydrogen atoms.

[8] The pharmaceutical composition according to any of [1]-[8], which further contains one, or two or more types of metal-containing compounds.

[9] The pharmaceutical composition according to [8], wherein the metal-containing compound is a compound containing iron, magnesium, zinc, nickel, vanadium, copper, chromium, molybdenum, or cobalt.

[10] The pharmaceutical composition according to [9], wherein the metal-containing compound is a compound containing iron, magnesium, or zinc.

[11] The pharmaceutical composition according to [10], wherein the metal-containing compound is a compound containing iron.

[12] The pharmaceutical composition according to [11], wherein said compound containing iron is sodium ferrous citrate.

[13] The use of the compound shown by the following Formula (I):

[Chemical Formula 2]

$R^1$—$NHCH_2COCH_2CH_2COOR^2$ (I), (wherein $R^1$ represents a hydrogen atom or an acyl group, and $R^2$ represents a hydrogen atom, a linear or branched alkyl group, a cycloalkyl group, an aryl group, or an aralkyl group) or a salt or an ester thereof in the production of a medicament for enhancing the antitumor effect of an immune checkpoint inhibitor.

[14] A method for enhancing the antitumor effect of an immune checkpoint inhibitor, comprising administering the compound shown by the following Formula (I):

[Chemical Formula 3]

$R^1$—$NHCH_2COCH_2CH_2COOR^2$ (I), (wherein $R^1$ represents a hydrogen atom or an acyl group, and $R^2$ represents a hydrogen atom, a linear or branched alkyl group, a cycloalkyl group, an aryl group, or an aralkyl group)
or a salt or an ester thereof to a subject to which an immune checkpoint inhibitor is administered or being administered.

Note that an invention of any combination of one or more characteristics of the present invention described above is also encompassed by the scope of the present invention.

Effects of the Invention

According to the present invention, a pharmaceutical composition for enhancing the antitumor effect by an immune checkpoint inhibitor is provided.

DESCRIPTION OF EMBODIMENTS

Figure 1:
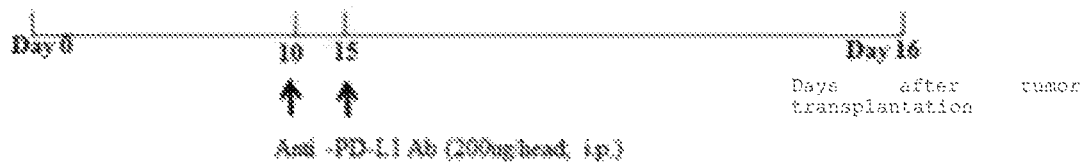
FIG. 1 shows the administration schedule of each test agent in the test of Example 1.

The present invention will now be described in detail.

The present invention relates to a pharmaceutical composition for enhancing the antitumor effect by an immune checkpoint inhibitor (hereinafter also referred to as "the pharmaceutical composition of the present invention").

An "immune checkpoint inhibitor" is an anticancer agent that suppresses the proliferation of cancer by binding to an immune checkpoint molecule which suppresses T cell activity due to presentation of antigen, and inhibiting its signal transduction. Immune checkpoint molecules may include both receptors and ligands which function as immune checkpoints.

In one embodiment of the present invention, an "immune checkpoint inhibitor" includes, but is not limited to, e.g. any antibody or compound that can inhibit the binding or interaction between PD-1L and PD-1, the binding or interaction between CD80/CD86 and CTLA4, the binding or interaction between CD137L and CD137, the binding or interaction between MHC and LAG-3/KIR, the binding or interaction between CD48 and CD244, the binding or interaction between GAL9 and TIM3, the binding or interaction between HVEM and BTLA/CD160, the binding or interaction between CD40L and CD40, the binding or interaction between OX40L and OX40, and the binding or interaction between GITRL and GITR.

In another embodiment of the present invention, an "immune checkpoint inhibitor" is selected from the group consisting of, but is not limited to, an anti-PD-1 antibody, an anti-PD-L1 antibody, an anti-CTLA4 antibody, an anti-B7 antibody, an anti-C27 antibody, an anti-KIR antibody, an IDO inhibitor, an anti-CD137 antibody, and an anti-TIM3 antibody.

In further another embodiment of the present invention, an "immune checkpoint inhibitor" is selected from, but is not limited to, atezolizumab, durvalumab, avelumab, nivolumab, pembrolizumab, pidilizumab, BMS-936559, ipilimumab, tremelimumab, enoblituzumab, varlilumab, lirilumab, epacadostat, utomilumab, urelumab, and TSR-022.

In further another embodiment of the present invention, an "immune checkpoint inhibitor" is an anti-PD-L1 antibody or an anti-PD-1 antibody.

The pharmaceutical composition of the present invention is characterized in that it has ALA or a derivative, salt, or ester thereof (hereinafter also simply referred to as "ALAs") as the active ingredient.

An ALA as used herein means 5-aminolevulinic acid. ALA is also referred to as δ-aminolevulinic acid, and is a type of amino acid.

The compound shown by the following Formula (I) can be exemplified as an ALA derivative. In Formula (I), $R^1$ represents a hydrogen atom or an acyl group, and $R^2$ represents a hydrogen atom, a linear or branched alkyl group, a cycloalkyl group, an aryl group, or an aralkyl group. Note that in Formula (I), ALA corresponds to when $R^1$ and $R^2$ are hydrogen atoms.

[Chemical Formula 4]

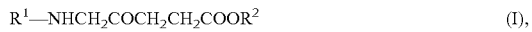

$$R^1\text{---}NHCH_2COCH_2CH_2COOR^2 \qquad (I),$$

ALAs may act as an active ingredient in vivo in the form of the ALA of Formula (I) or a derivative thereof, and can also be administered as a prodrug (precursor) that is degradated by an in vivo enzyme.

The acyl group in $R^1$ of Formula (I) can include a linear or branched alkanoyl group having 1-8 carbons such as formyl, acetyl, propionyl, butyryl, isobutyryl, valeryl, isovaleryl, pivaloyl, hexanoyl, octanoyl, and benzylcarbonyl groups, or an aroyl group having 7-14 carbons such as benzoyl, 1-naphthoyl, 2-naphthoyl groups.

The alkyl group in $R^2$ of Formula (I) can include a linear or branched alkyl group having 1-8 carbons such as methyl, ethyl, propyl, isopropyl, butyl, isobutyl, sec-butyl, tert-butyl, pentyl, isopentyl, neopentyl, hexyl, heptyl, and octyl groups.

The cycloalkyl group in $R^2$ of Formula (I) can include a cycloalkyl group having 3-8 carbons which may be saturated or have partially unsaturated bonds, such as cyclopropyl, cyclobutyl, cyclopentyl, cyclohexyl, cycloheptyl, cyclooctyl, cyclododecyl, and 1-cyclohexenyl groups.

The aryl group in $R^2$ of Formula (I) can include an aryl group having 6-14 carbons such as phenyl, naphthyl, anthryl, and phenanthryl groups.

The aralkyl group in $R^2$ of Formula (I) can be exemplified with the same aryl groups as above as the aryl moiety and the same alkyl groups as above as the alkyl moiety, and can specifically include an aralkyl group having 7-15 carbons such as benzyl, phenethyl, phenylpropyl, phenylbutyl, benzhydryl, trityl, naphthylmethyl, and naphthylethyl groups.

Preferred ALA derivative include compounds where $R^1$ is a formyl group, an acetyl group, a propionyl group, a butyryl group, and the like. Moreover, preferred ALA derivatives also include compounds where the above $R^2$ is a methyl group, an ethyl group, a propyl group, a butyl group, a pentyl group, and the like. Moreover, preferred ALA derivatives also include compounds where the combination of the above $R^1$ and $R^2$ is each combination of (formyl and methyl), (acetyl and methyl), (propionyl and methyl), (butyryl and methyl), (formyl and ethyl), (acetyl and ethyl), (propionyl and ethyl), and (butyryl and ethyl).

Among ALAs, a salt of ALA or a derivative thereof can include a pharmaceutically acceptable acid addition salt, a metal salt, an ammonium salt, an organic amine addition salt, and the like. Acid addition salts can be exemplified by e.g. each of inorganic acid salts such as a hydrochloride salt, a hydrobromide salt, a hydroiodide salt, a phosphate salt, a nitrate salt, and a sulfate salt, and each of organic acid addition salts such as a formate salt, an acetate salt, a propionate salt, a toluenesulfate salt, a succinate salt, an oxalate salt, a lactate salt, a tartrate salt, a glycolate salt, a methanesulfonate salt, a butyrate salt, a valerate salt, a citrate salt, a fumarate salt, a maleate salt, and a malate salt. Metal salts can be exemplified by each of alkali metal salts such as a lithium salt, a sodium salt, and a potassium salt, each of alkaline earth metal salts such as a magnesium salt and a calcium salt, and each of metal salts such as aluminum and zinc. Ammonium salts can be exemplified by e.g. ammonium salts and alkyl ammonium salts such as a tetramethylammonium salt. Organic amine salts can be exemplified by each of salts such as a triethylamine salt, a piperidine salt, a morpholine salt, and a toluidine salt. Note that these salts can also be employed as a solution at the time of use.

ALAs esters can include, but are not limited to, methyl esters, ethyl esters, propyl esters, butyl esters, pentyl esters, and the like.

Among the above ALAs, the most favorable are ALA and various esters such as an ALA methyl ester, an ALA ethyl ester, an ALA propyl ester, an ALA butyl ester, and an ALA pentyl ester, as well as hydrochloride salts, phosphate salts, and sulfate salts thereof. In particular, ALA hydrochloride salts and ALA phosphate salts can be exemplified as particularly favorable.

The above ALAs can be manufactured by e.g. well-known methods such as chemical synthesis, production by microorganisms, and production by enzymes. Moreover, the above ALAs may also form a hydrate or a solvate, and ALAs can be employed alone or in an appropriate combination of two or more.

When the above ALAs are to be prepared as an aqueous solution, attention must be paid so that the aqueous solution will not become alkaline in order to prevent degradation of ALAs. In the case it becomes alkaline, degradation can be prevented by removing oxygen.

In one embodiment, in the pharmaceutical composition of the present invention, one or more types of metal-containing compounds are used in combination. Accordingly, the pharmaceutical composition of the present invention can further contain one or more types of metal-containing compounds. The metal portion of such metal-containing compound can include iron, magnesium, zinc, nickel, vanadium, cobalt, copper, chromium, and molybdenum. In a preferred embodiment, the metal portion of the metal-containing compound is preferably iron, magnesium, or zinc, in particular iron.

In the present invention, the iron compound may be an organic salt or an inorganic salt. Inorganic salts can include ferric chloride, iron sesquioxide, iron sulfate, and ferrous pyrophosphate. Organic salts can include carboxylic salts such as a hydroxycarboxylic salt, citrate salts such as ferrous citrate, iron sodium citrate, sodium ferrous citrate (SFC), and iron ammonium citrate, organic acid salts such as ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminepentaacetate, iron sodium dicarboxymethylglutamate, iron ammonium dicarboxymethylglutamate, ferrous fumarate, iron acetate, iron oxalate, ferrous succinate, and iron sodium succinate citrate, as well as triethylenetetramine iron, lactoferrin iron, transferrin iron, sodium iron chlorophyllin, ferritin iron, saccharated iron oxide, and ferrous glycine sulfate.

In the present invention, the magnesium compound can include magnesium citrate, magnesium benzoate, magnesium acetate, magnesium oxide, magnesium chloride, magnesium hydroxide, magnesium carbonate, magnesium sulfate, magnesium silicate, magnesium nitrate, magnesium diammonium diethylenetriaminepentaacetate, magnesium disodium ethylenediaminetetraacetate, and magnesium protoporphyrin.

In the present invention, the zinc compound can include zinc chloride, zinc oxide, zinc nitrate, zinc carbonate, zinc sulfate, zinc diammonium diethylenetriaminepentaacetate, zinc disodium ethylenediaminetetraacetate, zinc protoporphyrin, and zinc-containing yeast.

The dosage of the metal-containing compound to a subject may be 0-100 folds by molar ratio to the dosage of ALA to the subject, desirably 0.01-10 folds, and more desirably 0.1-8 folds.

ALAs and the metal-containing compound contained in the pharmaceutical composition of the present invention can be administered as a composition comprising ALAs and the metal-containing compound or each can be administered alone, although it is preferred that even when administering each alone, they are administered at the same time. Same time here means not only administering simultaneously, but also even if not simultaneously, administering without substantial interval between each other so that the administration of ALAs and the metal-containing compound can exert additive effect, preferably synergistic effect.

The administration route of ALAs and the metal-containing compound in the present invention is not limited, and may be systemic administration or local administration. Administration routes can include, for example, oral administration including sublingual administration, or parenteral administration such as inhalation administration, intravenous administration including infusion, transdermal administration by e.g. patches, suppository, or administration by forced enteral nutrition employing nasogastric tube, nasointestinal tube, gastrostomy tube, or enterostomy tube. Moreover, as described above, ALAs and the metal-containing compound may be administered from separate routes.

The dosage form of the pharmaceutical composition of the present invention may be appropriately determined depending on the said administration route, and can include, but is not limited to, injections, infusions, tablets, capsules, fine granules, powders, liquids, solutions dissolved in syrups etc., patches, suppositories, and the like.

Other optional ingredients such as other medicinal ingredients, nutrients, and carriers can be added as necessary to the pharmaceutical composition according to the present invention. For example, as optional ingredients, various compounding ingredients for preparation of drugs such as pharmaceutically acceptable ordinary carriers e.g. crystalline cellulose, gelatin, lactose, starch, magnesium stearate, talc, vegetable and animal fat, oil, gum, and polyalkylene glycol, binders, stabilizers, solvents, dispersion mediums, expanders, excipients, diluents, pH buffers, disintegrants, solubilizers, solubilizing agents, and isotonic agents.

The administration subject of the pharmaceutical composition of the present invention is a subject to which an immune checkpoint inhibitor is administered or being administered, typically a subject suffering from cancer. The type of cancer to be the therapeutic subject may change depending on the immune checkpoint inhibitor used.

The dosage of ALAs to be administered by the pharmaceutical composition of the present invention, depending on the height, weight, age, and the symptom of the subject, can be administered in the range of 1 mg-1,000 mg, preferably 5 mg-100 mg, more preferably 10 mg-30 mg, further preferably 15 mg-25 mg per kg of subject body weight, when converted into ALA (i.e. converted into mass of when $R^1$ and $R^2$ are hydrogen atoms in Formula (I)).

Appropriate number of administrations and the administration frequency for the pharmaceutical composition of the present invention can be suitably determined by those skilled in the art in consideration of the administration conditions of the immune checkpoint inhibitor used in combination (the administration interval, the number of administrations, and the duration of administration). In one embodiment of the present invention, the pharmaceutical composition of the present invention is administered every day from before administration of, at the time of administration of, or after administration of the immune checkpoint inhibitor.

In the present invention, the effective amount of each of the pharmaceutical composition of the present invention and the immune checkpoint inhibitor can be administered to a subject at the same time or at different times, continuously or with intervals. The pharmaceutical composition of the present invention and the immune checkpoint inhibitor may be administered to a tumor patient in the same administration cycle, or each may be administered in different administration cycles. In one embodiment of the present invention, each of the pharmaceutical composition of the present invention and the immune checkpoint inhibitor are administered in different administration cycles.

In one embodiment of the present invention, the administration of the pharmaceutical composition of the present invention to a subject is initiated before the administration of the immune checkpoint inhibitor is initiated. For example, the pharmaceutical composition of the present invention can be administered every day from one week before the administration of the immune checkpoint inhibitor is initiated.

In another embodiment of the present invention, the administration of the pharmaceutical composition of the present invention to a subject is initiated on the same day as the administration of the immune checkpoint inhibitor. For example, the pharmaceutical composition of the present invention can be administered every day from the day the administration of the immune checkpoint inhibitor is initiated. When the pharmaceutical composition of the present invention and the immune checkpoint inhibitor are simultaneously administered, they may be prepared and administered as a single formulation, or may be simultaneously administered in separate administration routes.

In further another embodiment of the present invention, the administration of the pharmaceutical composition of the present invention to a subject is initiated after the administration of the immune checkpoint inhibitor. For example, the pharmaceutical composition of the present invention can be administered every day after the administration of the immune checkpoint inhibitor. As long as the antitumor effect by the immune checkpoint inhibitor can be enhanced, the time point of initiating the pharmaceutical composition of the present invention is not particularly limited, and it is preferred that an extended period of time, for example one month or longer, preferably three weeks or longer, more preferably two weeks of longer, and more preferably ten days or longer has not elapsed since the time point of initiating the immune checkpoint inhibitor.

The terms used herein, except for those that are particularly defined, are employed for describing particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

The present invention will now be described in further detail with reference to Examples. However, the present invention can be embodied by various aspects, and shall not be construed as being limited to the Examples described herein.

EXAMPLES

<Example 1> Enhancement of Antitumor Effect by Combination Use of ALA and PD-L1 Antibody Experimental Method To C57BL/6 mice, $3 \times 10^5$ of mouse melanoma cell strain B16F10 were inoculated in the flank, and the tumor was allowed to grow for 28 days. On Day 10 and Day 15 from inoculation, 200 µg/head of anti-mouse PD-L1 antibody (Clone: MIH5) was intraperitoneally administered for the PD-L1 antibody only administration group, the anti-PD-L1 antibody+ALA administration group, and the anti-PD-L1 antibody+ALA+SFC administration group (FIG. 1). For the anti-PD-L1 antibody+ALA+SFC administration group, 100 mg/kg of ALA hydrochloride salt (from neo ALA CO., LTD.) and 157 mg/kg of sodium ferrous citrate (SFC; from KOMATSUYA CORPORATION) were orally administered once a day from Day 10 to Day 16 from inoculation. Moreover, for the anti-PD-L1 antibody+ALA administration group, 100 mg/kg of ALA hydrochloride salt (from neo ALA CO., LTD.) was orally administered once a day from day 10 to day 16 from inoculation. The group with no treatment after inoculation was placed as the control group.

The tumor diameter was measured every two days, and v wherein v=(minor axis, mm)$^2$×(major axis, mm)/2 was recorded as the tumor volume (mm$^3$). The values of N were 13 mice for the control group (8 mice were alive on Day 16), 10 mice for the anti-PD-L1 antibody only group (9 mice were alive on Day 16), 4 mice for the anti-PD-L1 antibody+ALA administration group (all mice were alive on Day 16), and 9 mice for the anti-PD-L1 antibody+ALA+SFC administration group (all mice were alive on Day 16).

Result

Figure 2:
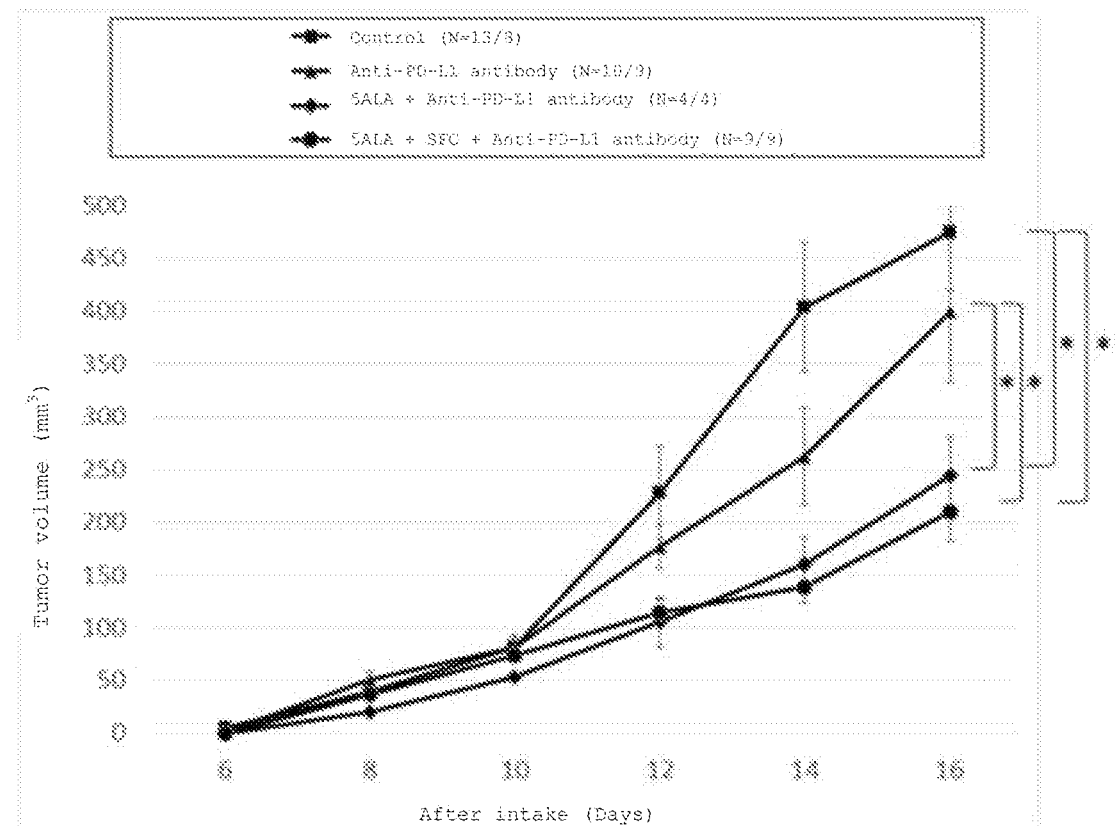
FIG. 2 shows the comparison among the non-treated group, the anti-PD-L1 antibody administration group, the anti-PD-L1 antibody+ALA administration group, and the anti-PD-L1 antibody+ALA+SFC administration group in the tumor volume after tumor inoculation. * shows that p<0.05 by t-test when the variances of the two populations are not equal.

On Day 16 from inoculation, the anti-PD-L1 antibody+ALA administration group had clearly smaller tumor volumes compared to the anti-PD-L1 antibody only group (FIG. 2). Moreover, the effect by the anti-PD-L1 antibody was more significant when ALA was added and SFC was further administrated (the anti-PD-L1 antibody+ALA+SFC administration group). This result indicates that the antitumor effect of the anti-PD-L1 antibody is enhanced by the combination use of ALA+SFC, and it is expected to contribute to further extension of mouse survival rates.

Figure 3:
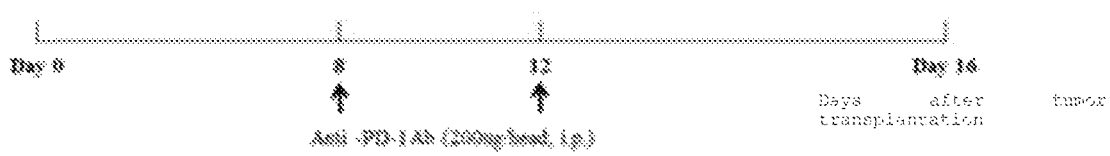
FIG. 3 shows the administration schedule of each test agent in the test of Example 2.

<Example 2> Enhancement of Antitumor Effect by Combination Use of ALA and PD-1 Antibody Experimental Method To C57BL/6 mice, $3 \times 10^5$ of mouse melanoma cell strain B16F10 were inoculated in the flank, and the tumor was allowed to grow for 16 days. On Day 8 and Day 12 from inoculation, 200 µg/mouse of anti-mouse PD-1 antibody (Clone: RMP1-14) was intraperitoneally administered for the PD-1 antibody only administration group, the anti-PD-1 antibody+ALA administration group, and the anti-PD-1 antibody+ALA+SFC administration group (FIG. 3). For the anti-PD-1 antibody+ALA+SFC administration group, 100 mg/kg of ALA hydrochloride salt (from neo ALA CO., LTD.) and 157 mg/kg of sodium ferrous citrate (SFC; from KOMATSUYA CORPORATION) were orally administered once a day from Day 8 to Day 16 from inoculation. The group with no treatment after inoculation was placed as the control group.

The tumor diameter was measured every two days, and v wherein v=(minor axis, mm)$^2$×(major axis, mm)/2 was recorded as the tumor volume (mm$^3$). The values of N were 18 mice for the control group (10 mice were alive on Day 16), 10 mice for the anti-PD-1 antibody only group (all mice were alive on Day 16), and 10 mice for the anti-PD-1 antibody+ALA+SFC administration group (9 mice were alive on Day 16).

Result

Figure 4:
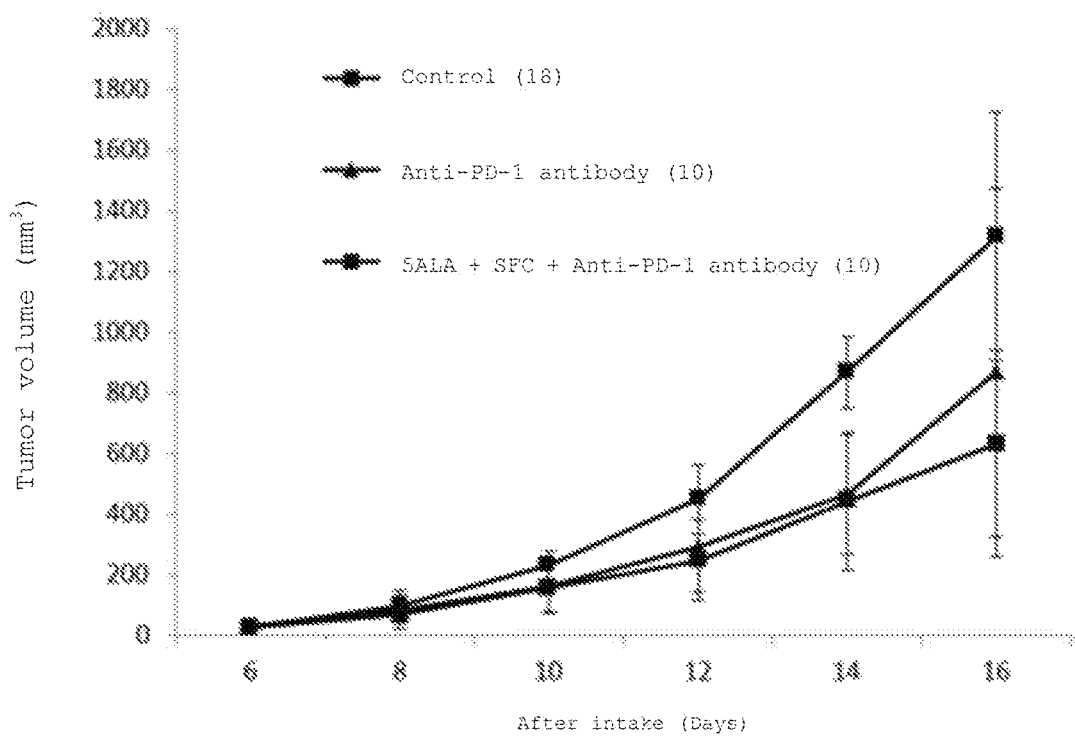
FIG. 4 shows the comparison among the non-treated group, the anti-PD-1 antibody administration group, and the anti-PD-1 antibody+ALA+SFC administration group in the tumor volume after tumor inoculation.

On Day 16 from inoculation, the anti-PD-1 antibody+ALA+SFC administration group had clearly smaller tumor volumes compared to the anti-PD-1 antibody only group (FIG. 4). This result indicates that the antitumor effect of the anti-PD-1 antibody is enhanced by the combination use of ALA+SFC, and it is expected to contribute to further extension of mouse survival rates.

INDUSTRIAL APPLICABILITY

According to the present invention, a pharmaceutical composition for enhancing the antitumor effect by an immune checkpoint inhibitor is provided. Accordingly, by using an immune checkpoint inhibitor and the pharmaceutical composition according to the present invention in combination, it is expected to lead to extension of life and increase of remission rate for cancer patients.

Moreover, since ALAs which are the active ingredient of the pharmaceutical composition according to the present invention is a type of natural amino acids contained in vivo that exists widely in animals, plants, and fungi etc., it has the advantage of being able to be used safely in vivo.

The invention claimed is:

1. A method for enhancing antitumor effect of an immune checkpoint inhibitor, the method comprising administering to a subject the immune checkpoint inhibitor; and systemically administering to the subject a compound of Formula (I):

$$R^1\text{—NHCH}_2\text{COCH}_2\text{CH}_2\text{COOR}^2 \qquad \text{[Chemical Formula I]}$$

wherein $R^1$ is a hydrogen atom and $R^2$ is a hydrogen atom, and wherein the immune checkpoint inhibitor is an anti-PD-L1 antibody or an anti-PD-1 antibody, thereby enhancing antitumor effect of the immune checkpoint inhibitor.

2. The method according to claim 1, wherein the systemically administering comprises systemically administering a pharmaceutical composition comprising a pharmaceutically acceptable carrier and the compound of Formula (I).

3. The method according to claim 1, wherein the compound of Formula (I) is administered to the subject at the same time as the immune checkpoint inhibitor.

4. The method according to claim 1, further comprising administering sodium ferrous citrate.

5. The method according to claim 1, wherein the compound of Formula (I) is administered to the subject at a different time than the immune checkpoint inhibitor.

6. The method according to claim 1, wherein the antitumor effect is a reduction in tumor volume and the method provides a greater reduction in tumor volume than the reduction in tumor volume achieved from administration of the immune checkpoint inhibitor alone.

* * * * *